(12) United States Patent
Li et al.

(10) Patent No.: US 6,269,501 B1
(45) Date of Patent: Aug. 7, 2001

(54) METHODS AND APPARATUS FOR AUTOMATIC PATIENT POSITIONING

(75) Inventors: Jianying Li, New Berlin; Thomas L. Toth, Brookfield, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/472,254

(22) Filed: Dec. 27, 1999

(51) Int. Cl.[7] .............................. A61B 6/02; A47B 13/00
(52) U.S. Cl. ................... 5/601; 378/20; 378/209; 600/415
(58) Field of Search .................... 5/601; 378/20, 378/177, 209; 250/363.02; 600/410, 415

(56) References Cited

U.S. PATENT DOCUMENTS

| | | | |
|---|---|---|---|
| 4,842,259 | * | 6/1989 | Rice ........................................ 5/601 |
| 5,457,724 | | 10/1995 | Toth . |
| 5,657,498 | * | 8/1997 | Hum ........................................ 5/601 |
| 6,148,058 | * | 11/2000 | Dobbs ..................................... 378/19 |
| 6,173,032 | * | 1/2001 | Besson .................................... 378/19 |
| 6,185,271 | * | 2/2001 | Kinsinger ............................... 378/19 |

* cited by examiner

*Primary Examiner*—Michael F. Trettel
(74) *Attorney, Agent, or Firm*—Armstrong Teasdale LLP; Christian G. Cabou

(57) ABSTRACT

In one aspect, the present invention is a method for automatically positioning an object, such as a patient, on a movable table using pre-scan scout data. High and low edges and a center of the object are determined as a function of object position in a z-axis direction. At least one threshold is determined from which to determine whether to move the table. The table is automatically repositioned based on comparison of the thresholds to respective distances of the high edge, low edge and center of the object from isocenter. The above described method allows automatic and dynamic adjustment of the table height to a position that prevents over-range while allowing use of higher gains to reduce image noise.

25 Claims, 2 Drawing Sheets

METHODS AND APPARATUS FOR AUTOMATIC PATIENT POSITIONING

BACKGROUND OF THE INVENTION

This invention relates generally to computed tomography (CT) imaging and, more particularly, to methods and apparatus for automatically positioning a patient for scanning using pre-scan scout data.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounstifield units", which are used to control the brightness of a corresponding pixel on a cathode ray tube display.

An over-ranged signal during data acquisition can cause image artifacts. Nevertheless it is desirable to apply higher gains in data acquisition to minimize electronic noise. Because over-ranging is most likely to occur in the center of the detector, it is possible to eliminate over-range by ensuring that the patient blocks an area of the detector center. It is difficult, however, to center the patient on a table for scanning. Because of different sizes and shapes at different body locations, it is particularly difficult to center all body parts simultaneously and sufficiently to prevent over-range at the detector center. It would be desirable to provide a method for centering all of a patient's body parts during scanning to prevent over-ranging.

BRIEF SUMMARY OF THE INVENTION

There is therefore provided, in one embodiment of the present invention, a method for automatically positioning an object, such as a patient, on a movable table using pre-scan scolut data. High and low edges and a center of the object are determined as a function of the location of the object in a z-axis direction. At least one threshold is determined from which to determine whether to move the table. The table is automatically repositioned based on comparison of the thresholds to respective distances of the high edge, low edge and center of the object from isocenter.

The above described method allows automatic and dynamic adjustment of the table height to a position that prevents over-range while allowing use of higher gains to reduce image noise.

DETAILED DESCRIPTION OF THE INVENTION

Figure 1:
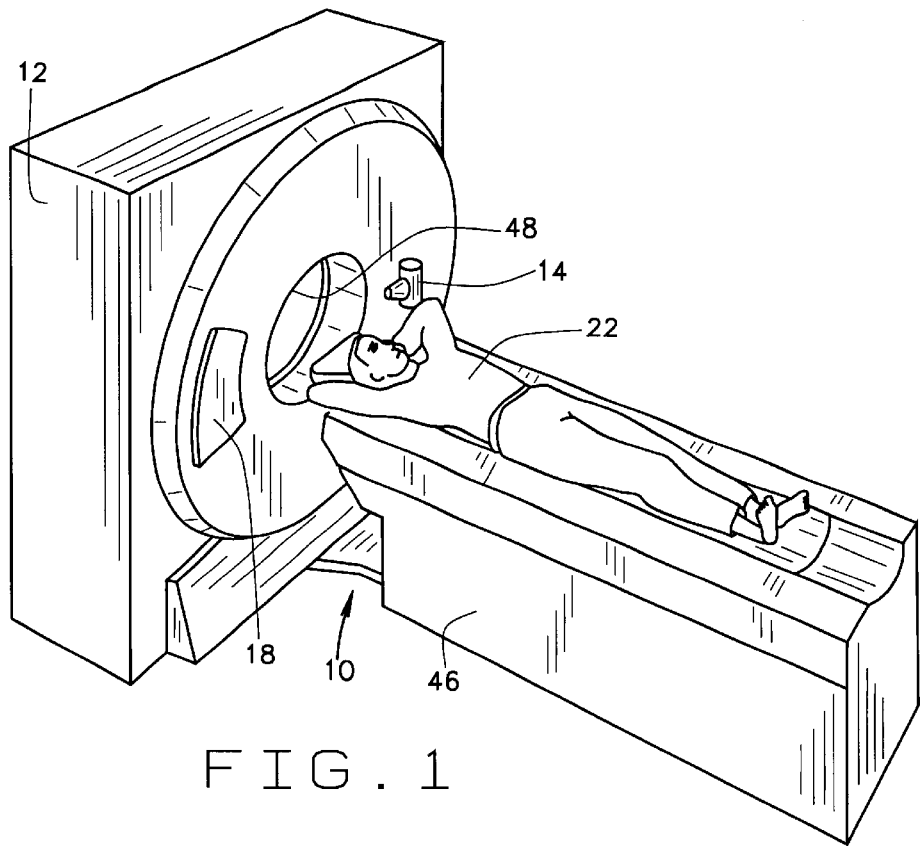
FIG. 1 is a pictorial view of a CT imaging system.
Figure 2:
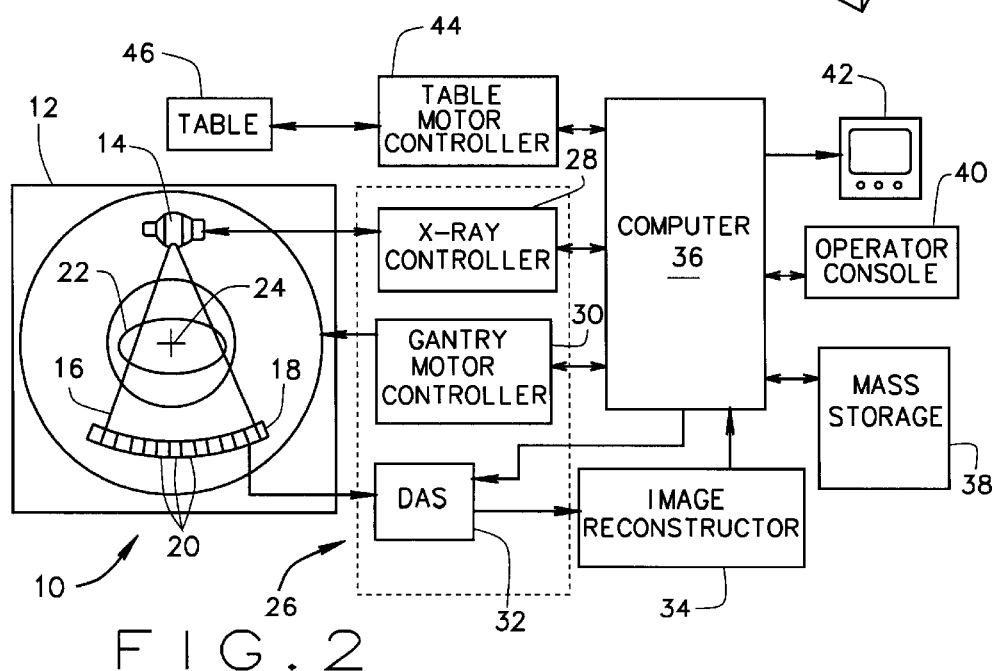
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation, or isocenter 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38.

Computer 36 also receives commands and scanning parameters from an operator viaconsole 40 that has a keyboard. An associated cathode ray tube display 42 allows the operator to observe the reconstructed image and other data from computer 36. the operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. Table 46 is moveable through gantry opening 48 along a z-axis direction.

Figure 3:
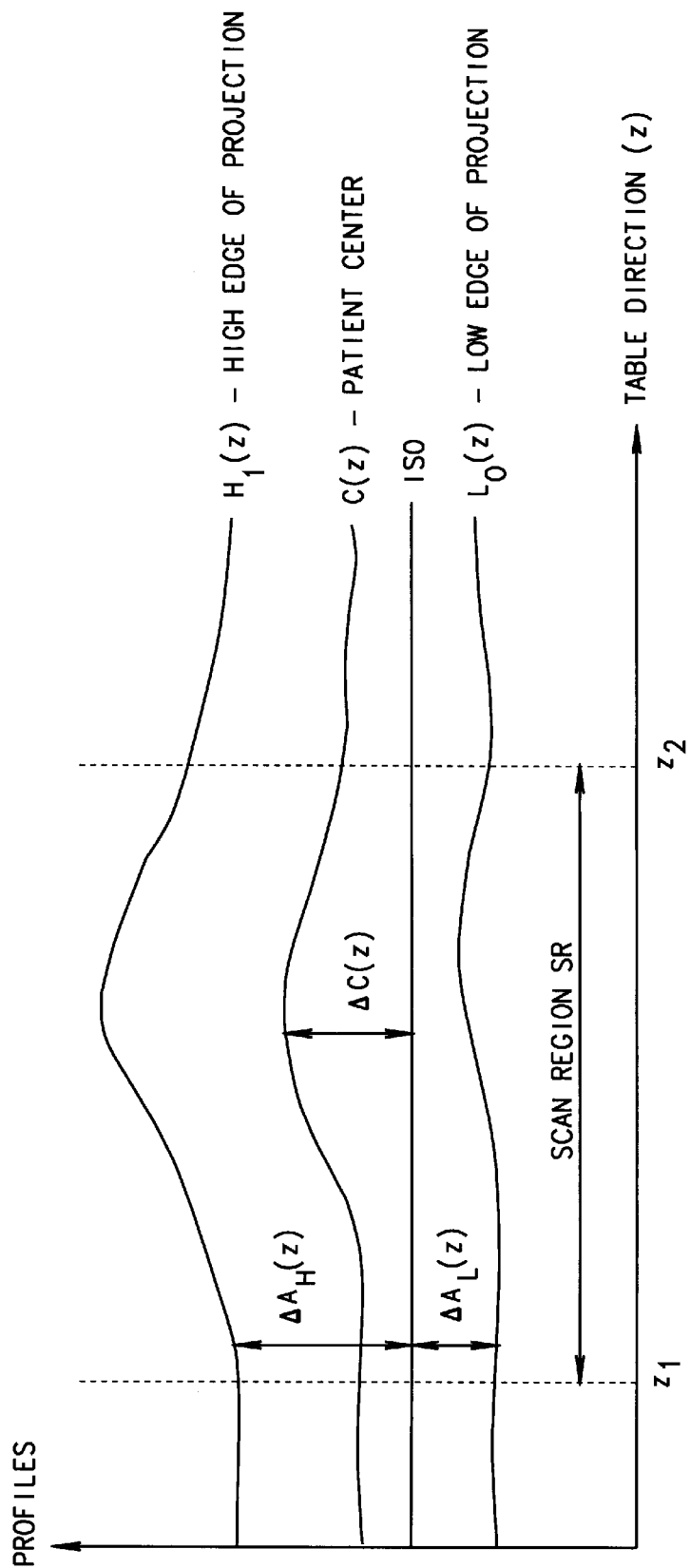
FIG. 3 is a graph illustrating center, high and low edges of a patient as functions of table z-direction.

In one embodiment, a method for automatically positioning a patient for scanning includes scout scanning patient 22 before performing regular scans. As shown in FIG. 3, high and low edges of patient 22 Hi(z) and Lo(z), respectively, are determined from scout scan data. Patient 22 center C(z) also is determined in each projection. Hi(z), Lo(z) and C(z) are determined as functions of table position in the z-axis direction. A scan region SR also is determined from scout scan data and is shown in FIG. 3, for example, between table positions $z_1$ and $z_2$.

Imaging system 10 then determines a distance $\Delta C(z)$ between patient 22 center C(z) and isocenter, 24, a distance $\Delta A_H(z)$ between patient 22 high edge Hi(z) and isocenter 24, and a distance $\Delta A_L(z)$ between patient 22 low edge Lo(z) and isocenter 24 in accordance with:

$$\Delta C(z)=C(z)-ISO \quad z_1<z<z_2$$

$$\Delta A_H(z)=Hi(z)-ISO \quad z_1<z<z_2$$

$$\Delta A_L(z)=ISO-Lo(z) \quad z_1<z<z_2$$

where $z_1$ and $z_2$ represent limits of scan region SR and ISO represents isocenter 24. A maximum of distance $\Delta C(z)$ and minimums of distances $\Delta A_H(z)$ and $\Delta A_L(z)$ then are determined in accordance with:

$$\Delta C(max)=MAX(\Delta C(z))$$

$$\Delta A_H(min)=MIN(\Delta A_H(z))$$

$$\Delta A_L(min)=MIN(\Delta A_L(z)).$$

Thresholds $V_1$ and $V_2$ then are determined from preset DAS 32 gains and are used to determine, for example, whether to move patient 22 and by how much, in accordance with:

IF $\Delta C(max)<V_1$ THEN do not move, ELSE

IF $\Delta A_H(min)>V_2$ AND $\Delta A_L(min)>V_2$ THEN do not move, ELSE

IF $\Delta A_H(min)<V_2$ THEN move table UP by $(V_2-\Delta A_H(min))$

IF $\Delta A_L(min)<V_2$ THEN move table DOWN by $(V_2-\Delta A_L(min))$.

After table 46 has been moved, the truth or falsity of the following comparison again is determined:

IF $\Delta A_H(min)>V_2$ AND $\Delta A_L(min)>V_2$

If the foregoing statement is not true, then it may be advisable to divide scan region SR into sub-regions, each sub-region having its own appropriate threshold values.

The above-described method is used in one embodiment to constantly move table 46 in an up-and-down, i.e., a y-axis, direction during scanning so that patient 22 is always centered. In another embodiment, a scan region is divided into sub-regions requiring different table heights. Appropriate threshold values then are selected, so that table height is kept constant over a particular scan sub-region while maintaining optimal patient position. Different images then are reconstructed in accordance with table motion to produce an image set (not shown) aligned in the y-axis direction as though the table had not been moved. The above described embodiment can also be used to adjust patient left and right positioning to ensure centering when the patient is positioned on his or her side. The above-described embodiment allows use of higher DAS gains to reduce image noise while avoiding over-ranging.

Although particular embodiments of the invention have been described and illustrated in detail, it is to be clearly understood that the same is intended by way of illustration and example only and is not to be taken by way of limitation. Threshold values $V_1$ and $V_2$ are exemplary only, and in other embodiments, sets of threshold values or a single threshold value are used. The invention can be implemented using hardware, software, firmware, or combinations thereof. Although the invention has been described with reference to a CT system, the invention can be used with other types of imaging systems. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan; however, the invention may be used with a helical scan. Accordingly, the spirit and scope of the invention are to be limited only by the terms of the appended claims and legal equivalents.

What is claimed is:

1. A method for operating an imaging system to image an object, the imaging system having an isocenter and including a table supporting the object, the table being movable in a z-axis direction, said method comprising the steps of:

determining an object high edge, an object low edge and an object center location as a function of object location in the z-axis direction;

determining at least one threshold from which to determine whether to move the table; and automatically repositioning the table based on comparison of the at least one threshold to respective distances of the object high edge, low edge and center from the isocenter.

2. A method in accordance with claim 1 wherein the step of automatically repositioning the table based on comparison of the at least one threshold to respective distances of the object high edge, low edge and center from the isocenter comprises the steps of:

determining a distance $\Delta C(z)$ between the object center C(z) and the isocenter ISO, a distance $\Delta A_H(z)$ between the object high edge Hi(z) and the isocenter ISO, and a distance $\Delta A_L(z)$ between the object low edge Lo(z) and the isocenter ISO, respectively in accordance with:

$$\Delta C(z)=C(z)-ISO \quad z_1<z<z_2$$

$$\Delta A_H(z)=Hi(z)-ISO \quad z_1<z<z_2$$

$$\Delta A_L(z)=ISO-Lo(z) \quad z_1<z<z_2$$

where $z_1$ and $z_2$ represent limits of a scan region; and determining a maximum $\Delta C(z)$, a minimum $\Delta A_H(z)$, and a minimum $\Delta A_L(z)$ in accordance with:

$$\Delta C(max)=MAX(\Delta C(z))$$

$$\Delta A_H(min)=MIN(\Delta A_H(z))$$

$$\Delta A_L(min)=MIN(\Delta A_L(z)).$$

3. A method in accordance with claim 2 wherein the at least one threshold includes thresholds $V_1$ and $V_2$, the table is movable in up- and down-directions, and said method further comprises the step of determining whether to move the table by comparing the thresholds $V_1$ and $V_2$ in accordance with:

IF $\Delta C(max)<V_1$ THEN do not move, ELSE

IF $\Delta A_H(min)>V_2$ AND $\Delta A_L(min)>V_2$ THEN do not move, ELSE

IF $\Delta A_H(min)<V_2$ THEN move table UP by $(V_2-\Delta A_H(min))$

IF $\Delta A_L(min)<V_2$ THEN move table DOWN by $(V_2-\Delta A_L(min))$.

4. A method in accordance with claim 3 further comprising the step of determining whether to divide the scan region into sub-regions by comparing, after table movement, in accordance with:

IF $\Delta A_H(min)>V_2$ AND $\Delta A_L(min)>V_2$.

5. A method in accordance with claim 3 further comprising repositioning the table in the up- and down-directions constantly during scanning.

6. A method in accordance with claim 3 further comprising dividing the scan region into sub-regions.

7. A method in accordance with claim 6 further comprising keeping the table at a constant height over a sub-region.

8. A method in accordance with claim 7 further comprising the step of reconstructing an image in accordance with table motion.

9. A method in accordance with claim 8 wherein the image is reconstructed from an image set aligned in the up- and down-directions.

10. A method in accordance with claim 1 wherein determining an object high edge, an object low edge and an object center location in the z-axis direction comprises the step of performing a scout scan of the object.

11. A method in accordance with claim 10 wherein the step of automatically repositioning the table based on comparison of the at least one threshold to respective distances of the object high edge, low edge and center from the isocenter comprises the steps of:

determining a distance $\Delta C(z)$ between the object center $C(z)$ and the isocenter ISO, a distance $\Delta A_H(z)$ between the object high edge $Hi(z)$ and the isocenter ISO, and a distance $\Delta A_L(z)$ between the object low edge $Lo(z)$ and the isocenter ISO, respectively in accordance with:

$$\Delta C(z) = C(z) - ISO \quad z_1 < z < z_2$$

$$\Delta A_H(z) = Hi(z) - ISO \quad z_1 < z < z_2$$

$$\Delta A_L(z) = ISO - Lo(z) \quad z_1 < z < z_2$$

where $z_1$ and $z_2$ represent limits of a scan region; and determining a maximum $\Delta C(z)$, a minimum $\Delta A_H(z)$, and a minimum $\Delta A_L(z)$ in accordance with:

$$\Delta C(\max) = \text{MAX}(\Delta C(z))$$

$$\Delta A_H(\min) = \text{MIN}(\Delta A_H(z))$$

$$\Delta A_L(\min) = \text{MIN}(\Delta A_L(z)).$$

12. A method in accordance with claim 11 wherein the at least one threshold comprises thresholds $V_1$ and $V_2$, the table is movable in up- and down-directions, and said method further comprises the step of determining whether to move the table by comparing the thresholds $V_1$ and $V_2$ in accordance with:

IF $\Delta C(\max) < V_1$ THEN do not move, ELSE

IF $\Delta A_H(\min) > V_2$ AND $\Delta A_L(\min) > V_2$ THEN do not move, ELSE

IF $\Delta A_H(\min) < V_2$ THEN move table UP by $(V_2 - \Delta A_H(\min))$

IF $\Delta A_L(\min) < V_2$ THEN move table DOWN by $(V_2 - \Delta A_L(\min))$.

13. A method in accordance with claim 1 wherein the imaging system is configured to apply gains in data acquisition and the at least one threshold is established in accordance with acquisition gain.

14. A method in accordance with claim 1 further comprising the step of repositioning the object based upon a comparison of the at least one threshold to distances of the object high edge, low edge and center from the isocenter.

15. An imaging system comprising a movable table having a z-axis direction of movement, said table configured to support an object for scanning, said imaging system having an isocenter and being configured to:

determine an object high edge, an object low edge and an object center location as a function of object location in said z-axis direction;

determine at least one threshold from which to determine whether to move said table; and automatically reposition said table based on comparison of the at least one threshold to respective distances of the object high edge, low edge and center from said isocenter.

16. A system in accordance with claim 15 wherein said system being configured to automatically reposition said table based on comparison of the at least one threshold to respective distances of the object high edge, low edge and center from said isocenter comprises said system being configured to:

determine a distance $\Delta C(z)$ between the object center $C(z)$ and said isocenter ISO, a distance $\Delta A_H(z)$ between the object high edge $Hi(z)$ and said isocenter ISO, and a distance $\Delta A_L(z)$ between the object low edge $Lo(z)$ and said isocenter ISO, respectively in accordance with:

$$\Delta C(z) = C(z) - ISO \quad z_1 < z < z_2$$

$$\Delta A_H(z) = Hi(z) - ISO \quad z_1 < z < z_2$$

$$\Delta A_L(z) = ISO - Lo(z) \quad z_1 < z < z_2$$

where $z_1$ and $z_2$ represent limits of a scan region; and determine a maximum $\Delta C(z)$, a minimum $\Delta A_H(z)$, and a minimum $\Delta A_L(z)$ in accordance with:

$$\Delta C(\max) = \text{MAX}(\Delta C(z))$$

$$\Delta A_H(\min) = \text{MIN}(\Delta A_H(z))$$

$$\Delta A_L(\min) = \text{MIN}(\Delta A_L(z)).$$

17. A system in accordance with claim 16 wherein the at least one threshold comprises thresholds $V_1$ and $V_2$, said table comprises up- and down-directions of movement and said system is further configured to determine whether to move said table by comparing the thresholds $V_1$ and $V_2$ in accordance with:

IF $\Delta C(\max) < V_1$ THEN do not move, ELSE

IF $\Delta A_H(\min) > V_2$ AND $\Delta A_L(\min) > V_2$ THEN do not move, ELSE

IF $\Delta A_H(\min) < V_2$ THEN move table UP by $(V_2 - \Delta A_H(\min))$

IF $\Delta A_L(\min) < V_2$ THEN move table DOWN by $(V_2 - \Delta A_L(\min))$.

18. A system in accordance with claim 17 further configured to reposition said table in said up- and down-directions constantly during scanning.

19. A system in accordance with claim 17 further configured to keep said table at a constant height over a sub-region.

20. A system in accordance with claim 17 further configured to reconstruct an image in accordance with table motion.

21. A system in accordance with claim 17 further configured to reconstruct an image from an image set aligned in the up- and down-directions.

22. A system in accordance with claim 15 wherein said system being configured to determine an object high edge, an object low edge and an object center location in said z-axis direction comprises said system being configured to perform a scout scan of the object.

23. A system in accordance with claim 22 wherein said system being configured to automatically reposition said table based on comparison of the at least one threshold to respective distances of the object high edge, low edge and center from said isocenter comprises said system being configured to:

determine a distance $\Delta C(z)$ between the object center $C(z)$ and said isocenter ISO, a distance $\Delta A_H(z)$ between the object high edge $Hi(z)$ and said isocenter ISO, and a distance $\Delta A_L(z)$ between the object low edge $Lo(z)$ and said isocenter ISO, respectively in accordance with:

$$\Delta C(z) = C(z) - ISO \quad z_1 < z < z_2$$

$$\Delta A_H(z) = Hi(z) - ISO \quad z_1 < z < z_2$$

$$\Delta A_L(z) = ISO - Lo(z) \quad z_1 < z < z_2$$

where $z_1$ and $z_2$ represent limits of a scan region; and determine a maximum $\Delta C(z)$, a minimum $\Delta A_H(z)$, and a minimum $\Delta A_L(z)$ in accordance with:

$$\Delta C(max) = MAX(\Delta C(z))$$

$$\Delta A_H(min) = MIN(\Delta A_H(z))$$

$$\Delta A_L(min) = MIN(\Delta A_L(z)).$$

24. A system in accordance with claim 23 wherein the at least one threshold comprises thresholds $V_1$ and $V_2$, said table comprises up- and down-directions of movement and said system is further configured to determine whether to move said table by comparing the thresholds $V_1$ and $V_2$ in accordance with:

IF $\Delta C(max) < V_1$ THEN do not move, ELSE

IF $\Delta A_H(min) > V_2$ AND $\Delta A_L(min) > V_2$ THEN do not move, ELSE

IF $\Delta A_H(min) < V_2$ THEN move table UP by $(V_2 - \Delta A_H(min))$

IF $\Delta A_L(min) < V_2$ THEN move table DOWN by $(V_2 - \Delta A_L(min))$.

25. A system in accordance with claim 15 configured to apply gains in data acquisition and establish the at least one threshold in accordance with data acquisition gains.

\* \* \* \* \*